United States Patent [19]

Morrison, Jr. et al.

[11] 4,255,427

[45] Mar. 10, 1981

[54] SUBSTITUTED PYRIMIDO (4,5-C)PYRIDAZINES

[75] Inventors: Robert W. Morrison, Jr.; William R. Mallory; Virgil L. Styles, all of Raleigh, N.C.

[73] Assignee: Burroughs Wellcome Co., Research Triangle Park, N.C.

[21] Appl. No.: 922,544

[22] Filed: Jul. 7, 1978

[30] Foreign Application Priority Data

Jul. 8, 1977 [GB] United Kingdom ............... 28764/77

[51] Int. Cl.³ .................. C07D 487/04; A61K 31/50; A61K 31/505
[52] U.S. Cl. .................................... 424/251; 544/236; 544/301; 544/320; 544/321; 544/323
[58] Field of Search ......................... 544/236; 424/251

[56] References Cited

U.S. PATENT DOCUMENTS 3,947,442   3/1976   Beckwith ............................ 544/236

OTHER PUBLICATIONS

Nakagome et al., "Chemical Abstracts", vol. 70, 1969, col. 4020z.
Minami et al., "Chemical Abstracts", vol. 84, 1976, col. 59531m.

*Primary Examiner*—Donald G. Daus
*Assistant Examiner*—James H. Turnipseed
*Attorney, Agent, or Firm*—Donald Brown

[57] ABSTRACT

This invention provides pyrimido (4,5-c)pyridazines, process for their preparation, veterinary compositions containing them and the preparation of such compositions. These pyrimido (4,5-c)pyridazines are useful in the treatment of coccidiosis.

20 Claims, No Drawings

SUBSTITUTED PYRIMIDO (4,5-C)PYRIDAZINES

This invention relates to pyrimido(4,5-c)pyridazines, methods of their preparation, compositions and formulations containing them, and their use in the treatment of coccidiosis.

The first pyrimido(4,5-c)pyridazines were disclosed by Pfleiderer and Ferch in 1958, *Ann. Chem.*, 615, 48 (1958) but no pharmacological activity was disclosed for these compounds which have the formula (O):

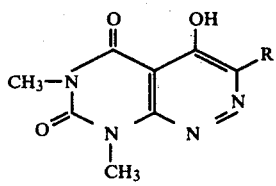

wherein R is a hydrogen atom or —$CO_2C_2H_5$ group. We have now discovered a group of pyrimido(4,5-c)pyridazines which are useful in the treatment of coccidiosis.

The present invention provides novel pyrimido-(4,5-c)pyridazines of formula (I), or their tautomers, or salts thereof,

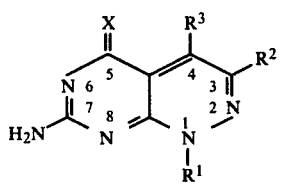

wherein $R^1$ is a benzyl group, or a lower alkyl group optionally substituted by a hydroxy group; $R^2$ is a hydrogen atom, a hydroxy group, a methyl group, a hydroxymethyl group, a benzyl group optionally substituted in the phenyl ring with a nitro group or one or two lower alkoxy groups, a phenacyl group optionally substituted in the phenyl ring with one or more hydroxy or lower alkoxy groups, a group $CH(Y)CO_2Z$ in which Y is a hydrogen atom, a lower alkyl group, or a benzyl group, and Z is a hydrogen atom or a lower alkyl group; $R^3$ is a hydroxy group, a methyl group, or a phenyl group optionally substituted with a hydroxy group; and X is an oxygen atom or a group NH; provided that (i) $R^3$ is a methyl group only when $R^2$ is a methyl or hydroxy group;
(ii) $R^2$ is a phenyl group optionally substituted with a hydroxy group only when $R^2$ is a hydrogen atom;
(iii) when $R^3$ is a hydroxy group, $R^2$ is other than a hydrogen atom;
(iv) $R^2$ and $R^3$ are not both hydroxy groups.

The term "lower" as used herein in conjunction with an alkyl or alkoxy group is indicative of the fact that such groups have from 1 to 4 carbon atoms arranged in a straight or branched chain. The expression "phenacyl group" however is used to denote solely a $C_6H_5COCH_2$— group.

It is to be understood that compounds where tautomerism is possible between, on the one hand, a hydroxy group and an oxo group, and on the other hand, an amino group and an imino group, at a particular position in either of the rings of the pyrimido(4,5-c)-pyridazines of formula (I), the more stable forms are respectively, the oxo group and the amino group. However, the general formulae used in the present specification do not necessarily represent the more stable forms of such pyridazines.

The above compounds of formula (I) have activity against coccidiosis either when used alone or in combination with a mixture of diaveridine and sulphaquinoxaline, such a mixture being known as an effective agent against coccidiosis. In particular, activity has been established against the organism *E. Tenella*, in in vitro and, in a number of instances, in vivo screens for compounds of formula (I) per se or with diaveridine and sulphaquinoxaline.

Those pyrimido(4,5-c)pyridazines which themselves have activity against *E. Tenella* are of formula (I), or their tautomers, or salts thereof, wherein $R^1$ is a lower alkyl group optionally substituted with a hydroxy group, or a benzyl group; $R^2$ is a hydrogen atom, a hydroxy group, a methyl group, a hydroxymethyl group, a benzyl group optionally substituted in the phenyl ring with a nitro or one or two lower alkoxy groups, a phenacyl group optionally substituted in the phenyl ring with one or more lower alkoxy groups, or a group $CH(Y)CO_2Z$ in which Y and Z are the same or different and each is a hydrogen atom or a lower alkyl group, and X is an oxygen atom or a group NH. Within this class there is a group of pyrimido(4,5-c)pyridazines which are particularly active and these have $R^1$ as a lower alkyl group, especially a methyl or n-butyl group; and $R^2$ as a hydrogen atom, a hydroxy group, a methyl group, a benzyl group optionally substituted in the phenyl ring with two methoxy groups, or a phenacyl group substituted in the phenyl ring with two methoxy groups. The most active compounds are 7-amino-1,3-dimethyl-4-oxo-5-hydroxy-1,4-dihydropyrimido(4,5-c)pyridazine; 7-amino-3-(3,4-dimethoxybenzyl)-5-hydroxy-1-methyl-4-oxo-1,4-dihydropyrimido(4,5-c)pyridazine; 7-amino-1-n-butyl-5-hydroxy-3-methyl-4-oxo-1,4-dihydropyrimido(4,5-c)-pyridazine; 5,7-diamino-1,3-dimethyl-4-oxo-1,4-dihydropyrimido(4,5-c)pyridazine; 7-amino-3-(3,4-dimethoxybenzoyl)-methyl-5-hydroxy-1-methyl-4-oxo-1,4-dihydropyrimido(4,5-c)-pyridazine; 7-amino-3-benzyl-5-hydroxy-1-methyl-4-oxo-1,4-dihydropyrimido(4,5-c)pyridazine; 7-amino-3-(2,4-dimethoxybenzoyl)methyl-5-hydroxy-1-methyl-4-oxo-1,4-dihydropyrimido(4,5-c)pyridazine; 7-amino-1,4-dimethyl-3,5-dioxo-1,2,3,5-tetrahydropyrimido-(4,5-c)pyridazine; 7-amino-5-oxo-1,3,4-trimethyl-1,5-dihydropyrimido(4,5-c)pyridazine; 7-amino-1-methyl-5-oxo-4-phenyl-1,5-dihydropyrimido(4,5-c)-pyridazine; and 7-amino-4-(4-hydroxyphenyl)-1-methyl-5-oxo-1,5-dihydropyrimido(4,5-c)pyridazine.

It has previously been stated that in 1958 Pfleiderer W. and Ferch H. (*Justus Liebig's Ann. Chem.*, 1958, 615, 48) reported the preparation of 4-hydroxy-6,8-dimethyl-pyrimido(4,5-c)pyridazine-5,7-(6H, 8H)-dione by the cyclisation of glyoxylic acid ethyl ester-1,3-dimethyluracil-(4)-hydrazone. It has now been found that this cyclisation reaction can surprisingly be extended to a novel class of intermediates which have a number of different substituents.

There has further been described in the literature Castle, et. al., *J. Het. Chem.*, 1975, 12, 1221) a reaction between 6-(α-methylhydrazino)-3-methyluracil and 2,3-butanedione which leads to 1,3,4,6-tetramethyl-pyrimido(4,5-c)pyridazine-5,7-(1H, 6H)-dione. Unexpectedly, pyrimido(4,5-c)pyridazines having different substituents and falling within the definition of formula (I) can be prepared by a modification of this reaction.

Thus the present invention further provides a method of preparing a compound of the formula (I), or a tautomer or salt thereof as hereinbefore defined, which comprises the cyclisation of a compound of the formula (II):

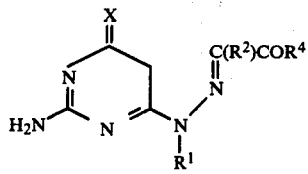
(II)

or a tautomer or salt thereof, wherein X, $R^1$ and $R^2$ are as hereinbefore defined and $R^4$ is a lower alkoxy group (to give compounds of the formula (I), where $R^3$ is OH) or a group $R^3$ as hereinbefore defined apart from a hydroxy group (to give compounds of formula (I) where $R^3$ is other than OH), and thereafter when X is an oxygen atom and $R^3$ is an acyloxymethyl group, optionally hydrolysin $R^3$ to a hydroxymethyl group.

The nature of the substituents on the pyrimidine ring of the compounds of the formula (II) is such that when $R^4$ is a lower alkoxy group, unlike the Pfleiderer and Ferch article, ring closure can apparently only be achieved when the nitrogen atom at the 6-position is substituted by $R^1$ as hereinbefore defined. Moreover this cyclisation reaction is particularly surprising since the report of Pfleiderer and Ferch teaches that such reactions only work for those hydrazone intermediates which have a glyoxylic acid alkyl ester substitution, yet a corresponding substitution in the present intermediates results in little, if any, pyrimido(4,5-c)pyridazine.

The cyclisation reaction may be carried out in any suitable solvent but will desirably be carried out in a hydroxylic solvent at a non-extreme temperature, i.e. between 10° C. and 110° C.; when $R^4$ is a lower alkoxy group the reaction is suitably carried out in glacial acetic acid, water or a $C_{1-4}$ alkanol, at reflux temperature for up to several days and is preferably carried out in refluxing methanol, or in ethanol at the reflux temperature of methanol. When $R^4$ is group $R^3$ the reaction is preferably carried out in refluxing water.

The conditions for hydrolysing the lower acyloxymethyl group to a hydroxymethyl group are preferably alkaline, for example aqueous sodium hydroxide, and the reaction may conveniently be performed at room temperature for 15 to 60 minutes, for example 30 minutes.

The compounds of the formula (II) and tautomers thereof can be prepared, preferably in situ, by condensing a 2-amino-6-hydrazinopyrimidine of the formula (III):

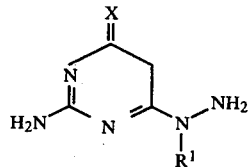
(III)

or a tautomer thereof with a compound of the formula: $R^2CO.CO.R^4$ wherein $R^1$, $R^2$, $R^4$ and X are as defined for formulae (I) and (II) above.

This reaction is suitably carried out under the same conditions as those used for the cyclisation reaction described above.

In the preparation of those compounds of the formula (I) wherein $R^2$ is a group $CH(Y)CO_2Z$ or a phenacyl group, some other bi-cyclic compound may be formed as a by-product. In such cases, it may be necessary to isolate the required compound by the usual procedures known in the art.

The compounds of the formulae (II) and (III) and novel and constitute further aspects of the present invention.

The compounds of formula (I) wherein $R^1$ is as hereinbefore defined, $R^3$ is a hydroxy group, X is an oxygen atom, and $R^2$ is a group $CH(Y)CO_2Z$ in which Y is as hereinbefore and Z is a lower alkyl group may be hydrolysed to give further compounds of formula (I) wherein $R^1$ is as hereinbefore defined, $R^3$ is a hydroxy group, X is an oxygen atom, and $R^2$ is a group $CH(Y)CO_2Z$ in which Y is as hereinbefore defined and Z is a hydrogen atom. The starting compounds of formula (I) may be prepared from the corresponding compounds of formula (II) as described previously.

The conditions for this reaction are preferably alkaline which may be achieved by using, for instance, aqueous sodium hydroxide, and the reaction may be conveniently performed at room temperature for 15 to 150 minutes, for example 90 minutes.

The compounds of formula (I) wherein $R^1$, $R^2$ and $R^3$ are as hereinbefore defined and X is a group NH may be hydrolysed to give further compounds of formula (I) which are correspondingly substituted except that X is an oxygen atom and that, in the case where $R^2$ in the starting material is a group $CH(Y)CO_2Z$ in which Z is a lower alkyl group, Z is a hydrogen atom. The starting compounds of formula (I) may be prepared from the corresponding compounds of formula (II) as described previously.

The conditions for this reaction are preferably alkaline which may be achieved by using, for instance, aqueous sodium hydroxide, and the reaction may be conveniently performed under reflux for 10 to 40 hours, for example 24 hours. However, it should be noted that during the course of this reaction some decarboxylation may take place possibly giving rise to small amounts of by-product which may necessitate subsequent separation by known techniques.

Compounds of formula (I) wherein $R^1$ is as hereinbefore defined, X is an oxygen atom, $R^3$ is a methyl group and $R^2$ is a hydroxy group can be prepared by the hydrolysis of a compound of formula (IV):

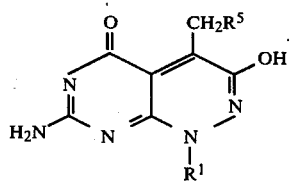
(IV)

wherein $R^1$ is as hereinbefore defined and $R^8$ is an aroyl group, preferably a benzoyl group, optionally substituted with one or more lower alkoxy groups, for example 3,4,5-trimethoxy substitution. Compounds of formula (IV) are novel and represent a further aspect of the present invention.

In turn they may be prepared by the cyclisation of a compound of formula (V):

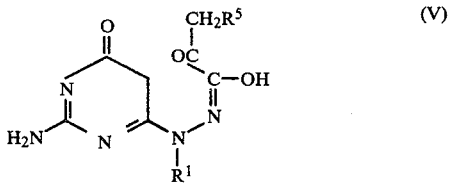

wherein $R^1$ and $R^5$ are as hereinbefore defined, the reaction preferably being performed under reflux in methyl cellosolve.

Compounds of formula (V) are novel and constitute yet another aspect of the present invention. Conveniently they are prepared, preferably in situ by the reaction of a compound of formula (III) wherein $R^1$ is as hereinbefore defined and X is an oxygen atom with a compound of the formula: $R^5CH_2.CO.CO.OR^6$ wherein $R^5$ is as hereinbefore defined and $R^6$ is a lower alkyl group, in methyl cellosolve, preferably under reflux.

All the starting materials specified above for the various syntheses may be prepared by standard methods taught in the art.

The present invention in a further aspect provides a composition for use in the treatment of coccidiosis which comprosition comprise non-toxic, effective anti-coccidial treatment amounts of each of diaveridine, sulphaquinoxaline and a compound of formula (I), or its tautomer, or a veterinary acceptable salt thereof, as hereinbefore defined, in particular such a compound wherein $R^1$ is a lower alkyl group optionally substituted with a hydroxy group, or a benzyl group; $R^2$ is a hydrogen atom, a hydroxy group, a methyl group optionally substituted in the phenyl ring with a nitro or one or two lower alkoxy groups, a carboxy group, a phenacyl group optionally substituted in the phenyl ring with one or more lower alkoxy groups, or a group $CH(Y)CO_2Z$ in which Y and Z are the same or different and each is a hydrogen atom or a lower alkyl group, and X is an oxygen atom or a group NH.

The above tripartite compositions are prepared by admixture of the requisite non-toxic anti-coccidial treatment amounts of each of the active ingredients.

The compounds of formula (I), their tautomers, and veterinary acceptable salts, or compositions thereof, may be presented in association with a carrier in veterinary formulations suitable for oral administration. Such formulations may be presented in discrete units, such as tablets, each containing a predetermined amount of the compound, but may also be presented as a powder, as granules, as a solution or suspension in an aqueous or non-aqueous liquid. Most conveniently, however, they may be presented as a poultry feed, at 5 to 500 ppm in the diet, with a preferred dose range of 150 to 300 ppm.

Accordingly, the present invention provides a poultry feed in which there is a composition as hereinbefore defined or a non-toxic effective anti-coccidial treatment amount of a compound of formula (I), their tautomers, or veterinary acceptable salts thereof.

Examples of veterinary acceptable salts are those derived from mineral or organic acids, for example hydrochloric acid, hydrobromic acid, sulphuric acid, acetic acid, citric acid, tartaric acid, lactic acid, maleic acid or salicyclic acid. Acid addition salts which are not veterinary acceptable may be rendered so by a conventional metathetical reaction. Further examples of veterinary acceptable salts are, in the case when $R^2$ in formula (I) is a carboxy group or a group $CH(Y)CO_2Z$ in which Z is a hydrogen atom, are alkali metal, for example sodium, salts.

In another aspect the present invention provides a method of treating poultry infected with coccidiosis which comprises administering a composition or a non-toxic effective anti-coccidial treatment amount of a compound of formula (I) hereinbefore defined, preferably administering a veterinary formulation or poultry feed as hereinbefore defined to the infected poultry.

Further advantages of the present invention can be ascertained from the following examples which should not be construed as limiting the scope of the invention in any way.

Example 1—6-(1-Methylhydrazino)isocytosine (III) ($R^1=CH_3$; X=O)

A mixture of 6-chloroisocytosine (17.50 g) and methylhydrazine (27.70 g) in water (900 ml) was stirred and refluxed for 3 hours. The resulting solution was allowed to stand at room temperature for 6 hours, then at 0° overnight, in order that the product could crystallise out. The white crystals were collected by filtration, washed with water (800 ml) and subsequently with 95% ethanol (200 ml). Drying under vacuum at 70° C. yielded 6-(1-methylhydrazino) isocytosine (11.01 g; 56% of theoretical yield; M.P. 274°-280° C. decomposition).

Elemental analysis: Calcd. for $C_5H_9N_5O.0.5H_2O$: C 36.58%, H 6.14%, N 42.66%. Found: C 36.42%, H 6.06%, N 42.61%.

NMR (DMSO-$d_6$) δ3.12 (s,3H), 4.47 (br s, 2H), 5.00 (s,1H), 6 16 (br s,2H), 9.68 (br s, 1H).

U.V. λmax ($CH_3OH$) 225.5 nm (ε24,000), 274 (17,300).

Example 2—6-(1-Ethylhydrazino)isocytosine (III) ($R^1=C_2H_5$; X=O)

A mixture of 6-chloroisocytosine (4.00 g) and ethylhydrazine (4.00 g) in water 980 ml) was refluxed for 1½ hours after which time the resulting solution was filteed while hot to remove dust particles, flushed with nitrogen, and sealed. The solution was then allowed to cool slowly to room temperature so that the product could crystallise out. The straw-coloured crystals were collected by filtration, washed with water and subsequently methanol. During under vacuum at 70° C. yielded 6-(1-ethyl hydrazino)isocytosine (2.83 g; 59% of theoretical yield;

M.P. 249°-250° C. decomposition).

Elemental analysis: Calcd. for $C_6H_{11}N_5O$: C 42.59%, H 6.55%, N 41.40% Found: C 42.33%, H 6.74%, N 41.18%.

NMR (DMSO-$d_6$) δ1.03 (t, 3H), 3.59 (q, 2H) 4.33 (br.s, 2H), 4.99 (s,1H), 6.15 (br s, 2H), 9.82 (br s, 1H)

U.V. λmax ($CH_3OH$) 226 nm (ε25,000), 273 (18,200).

EXAMPLE 3—6-[1-(2-Hydroxyethyl) hydrazino]isocytosine (III) ($R^1=CH_2CH_2OH$; X=O)

To a refluxing mixture of 6-chloroisocytosine (17.50 g) in water (300 ml) was added 2-hydroxyethylhydrazine (45.6 g). The resulting hazy solution became darker during further reluxing and after 1¾ hours it was filtered through Celite. The filtrate was then allowed to stand overnight at room temperature in order that crystallisation of the product could take place on cooling. The white crystals were collected by filtration, washed with water (100 ml) and subsequently methanol (100 ml). Drying under vacuum at 70° C. yielded 6-[1-(2-hydroxyethyl)hydrazino]isocytosine (12.02 g; 54% of theoretical yield; M.P. 232°–239° C. decomposition)

Elemental analysis: Calcd. for $C_6H_{11}N_5O_2$: C 38.91%, H 5.99%, N 37.82%. Found: C38.95%, H 6.08%, N 37.81%.

NMR (DMSO-$d_6$) δ3.61 (s,4H), 4.45 (br s,3H), 5.01 (s,1H), 6.17 (br s,2H), 9.75 (or s,1H).

U.V. λmax ($CH_3OH$) 224 nm (ε23,500), 272(16,700).

Example 4—6-(1-n-Butylhydrazino)isocytosine (III) ($R^1$=n-$C_4H_9$; X=O)

A mixture of 6-chloroisocytosine (17.50 g) and n-butylhydrazine (23.30 g) in water (900 ml) was stirred and refluxed for 4 hours. The resulting solution was allowed to stand at room temperature for 6 hours in order that the product could crystallise out. The tan crystals were collected by filtration and washed with water (175 ml). Drying overnight in a vacuum desiccator protected from light yielded 6-(1-n-butylhydrazino)isocytosine (18.43 g; 77% of theoretical yield; M.P. 208°–215° C. decomposition).

Elemental analysis: Calcd. for $C_8H_{15}N_5O$: C 48.71%, H 7.67%, N 35.51%. Found: C 48.76%, H 7.69% N 35.30%.

NMR (DMSO-$d_6$) δ0.6–1.8 (m, 7H), 3.58 (t,2H), 4.39(br s,2H), 5.05 (s,1H), 6.22 (br.s,2H), 9.85 (br s,1H).

U.V. λmax ($CH_3OH$) 227 nm (ε25,000), 274 (18,400).

Example 5—6-(1-Benzylhydrazino)isocytosine (III) ($R^1$=$CH_2C_6H_5$; X=O)

A mixture of 6-chloroisocytosine (17.50 g), triethylamine (90.10 g), and benzylhydrazine dihydrochloride (46.90 g) in water (900 ml) was refluxed for 10 minutes after which time the resulting solution was filtered to remove impurities present in the hydrazine salt. After refluxing the filtrate for 9 hours a white solid was collected by filtration from the hot reaction mixture, washed with water (250 ml) and dried overnight at room temperature in a vacuum desiccator protected from the light to yield 6-(1-benzylhydrazino)isocytosine (18.65 g; 67% of theoretical yield, M.P. 270°–290° C. decomposition).

Elemental analysis: Calcd. for $C_{11}H_{13}N_5O$: C 57.13%, H 5.67%, N 30.29%. Found: C 57.15%, H5.75%, N30.25%.

NMR (DMSO-$d_6$) δ4.34(br s,2H), 4.81(s,2H), 5.07 (s,1H),6.20 (br s,2H), 7.25 (s,5H), 9.80 (br s,1H).

U.V. λmax ($CH_3OH$) 226 nm (ε27,000), 275 (20,000).

Example 6—2,4-Diamino-6-(1-methylhydrazino)pyrimidine (III) ($R^1$=$CH_3$; X=NH)

To a refluxing solution of 6-chloro-2,4-diaminopyrimidine (4.0 g) in anhydrous methanol (40 ml) was added methylhydrazine (3.2 g). After 18 hours the refluxing mixture was allowed to cool to room temperature under a nitrogen atmosphere in order that the product could crystallise out. The white solid (3.0 g) was collected by filtration and dried under reduced pressure at 70° C. Recrystallisation of the product from methanol/methylhydrazine (50/1) gave straw-coloured crystals of 2,4-diamino-6-(1-methylhydrazino)pyrimidine (1.92 g; 56% of theoretical yield; M.P. 214°–217° C. decomposition).

Elemental analysis: Calcd. for $C_5H_{10}N_6$:C 38.95%, H 6.54%, N 54.51%. Found: C 38.99%, H 6.62%, N 54.38%.

NMR (DMSO-$d_6$)δ3.05(s,3H), 4.27 (br.s,2H), 5.40 (s,3H), 5.55 (br.s,2H).

U.V. λmax ($CH_3OH$) 219 nm (ε27,700) 277 (15,500).

Example 7—7-Amino-1,3-dimethylpyrimido[4,5-c]pyridazine-4,5(1H,6H)-dione (I) ($R^1$=$CH_3$;$R^2$=$CH_3$;$R^3$=OH; X=O)

To a stirred, refluxing solution of 6-(1-methylhydrazino)isocytosine hemihydrate (8.00 g) in water (1 L) was added methyl pyruvate (6.00 g). After 70 minutes a greenish-yellow solid was collected by filtration of the hot reaction mixture, washed with two portions of water (50 ml each) and dried under vacuum at 70° C. to yield 7-amino-1,3-dimethylpyrimido[4,5-c]pyridazine-4,5(1H,6H)-dione (5.11 g; 51% of theoretical yield; MP>300° C.).

Elemental analysis: Calcd. for $C_8H_9N_5O_2$: C 46.37%, H 4.38%, N 33.80%. Found: C 46.48%, H 4.42%, N 33.91%.

NMR (DMSO-$d_6$) 2.07(s,3H), 3.71(s,3H), 7.12 (br s,2H), 10.75 (br.s,H) pKa values 4.1±0.1; 8.6±0.1.

Example 8a—2-(N-(2,4-Diamino-6-pyrimidinyl)-N-methylhydrazono)propionaldehyde Oxime To 240 ml of glacial acetic acid that had been degassed of oxygen with nitrogen was added 8.00 g (0.0519 mol) of 2,4-diamino-6-(1-methylhydrazino)-pyrimidine and 5.42 g (0.0623 mol) of pyruvaldoxime. A positive nitrogen pressure was applied, and the initial mixture was stirred and heated in a 60° oil bath. After 2 hours 47 minutes the resulting solution was allowed to cool to room temperature and was filtered to remove a small amount of solid.

The filtrate was concentrated under vacuum at 45° to a yellow solid to which was added 400 ml of ethyl acetate. The solid was pulverized, collected, washed with 2×80 ml of ethyl acetate, and dried overnight under vacuum at 70°, yield 9.00 g of yellow solid shown by NMR to be desired product contaminated with acetic acid and little else. A 1.00 g sample of solid was recrystallised from ethyl acetate, yield 0.632 g (48%): MP 216° dec; NMR (DMSO-$d_6$) δ2.10(s, 3H), 3.25(s, 3H), 5.31(s, 1H), 5.72 and 5.92 (overlapping br s's, 4H), 7.87(s, 1H), 11.65(br s, 1H). A small amount of ethyl acetate was indicated; U.V. λmax ($CH_3OH$) 257 nm sh (ε11,300), 268 sh (10,500), 330.5 (5,800). Mass spectrum of a different batch (160°): M$^\pm$, m/e 223, 16%; m/e 179, 100%. An exact mass scan indicated the following accurate masses: 223.1183 ($C_8H_{13}N_7O$), 179.1047 ($C_7H_{11}N_6$).

Anal. Calcd. for $C_8H_{13}N_7O.0.06\ C_4H_8O_2$: C 43.30%; H 5.95%; N 42.91. Found: C 43.59%; H 6.01%; N 42.93%.

Example 8a—7-Amino-1,5-dihydro-5-imino-1,3-dimethylpyrimido(4,5-c)pyridazine Trifluoroacetate To 10 ml of stirred, refluxing trifluoroacetate acid was added 0.146 g (0.000654 mol) of 2-(N-(2,4-diamino-6-pyrimidinyl)-N-methylhydrazono)propionaldehyde oxime. After 2 hours 17 minutes the solution was allowed to cool to room temperature.

The solution was concentrated under vacuum at 40° to an orange residue to which was added a little methanol in order to esterify at least some residual trifluoroacetic acid. The methanol was removed under vacuum at 40°, and the residue was dissolved in 25 ml of ethyl acetate. Triethylamine was added to the solution until no more solid precipitated. Yellow solid was collected, washed with 2×2 ml of ethyl acetate, and dried under vacuum at 70° yield 0.099 g (49%): MP 232 dec; NMR (DMSO-d$_6$) δ2.56 (s, 3H), 4.14(s, 3H), 8.22 brs and 8.33 brs (2H), 8.63 (s, 1H), 8.85(br s, 2H). A small amount of ethyl acetate was indicated; UV of a different batch λmax (CH$_3$OH) 263.5 nm (ε16,500), 267 sh (16,000), 350 sh (3,700), 401.5(5,300).

Anal. Calcd. for $C_8H_{10}N_6 \cdot C_2HF_3O_2 \cdot 0.03 C_4H_8O_2 \cdot 0.20 OH_2O$: C 39.15%; H 3.78%; N 27.07%; F 18.36. Found: C 39.10%; H 3.74%; N 27.02%; F 18.29.

EXAMPLE 8a—5,7-Diamino-1,3-dimethylpyrimido(4,5-c)-pyridazin-4(1H)-one

To a solution of 0.049 g (0.00016 mol) of 7-amino-1,5-dihydro-5-imino-1,3-dimethylpyrimido(4,5-c)-pyridazine trifluoroacetate in 3 ml of water was added 0.022 g (0.00026 mol) of sodium bicarbonate, and the yellow solution was allowed to stand at room temperature while loosely covered and exposed to oxygen.

After 22 days precipitated yellowish-brown solid was collected, washed with water, and dried under vacuum at 70°, yield 0.018 g (≦54%). NMR, tlc, uv, and mass spectral data indicated this solid to be the same as that written up in Example 8 with the exception that some minor impurities were present.

EXAMPLE 8b—5,7-Diamino-1,3-dimethylpyrimido[4,5-c]-pyridazin-4(1H)-one (I) ($R^1$=CH$_3$;$R^2$=CH$_3$;$R^3$=OH; X=NH)

To a refluxing solution of 2,4-diamino-6-(1-methylhydrazino)-pyrimidine (500 mg) in anhydrous methanol (15 ml) was added methyl pyruvate (496 mg) over a five minute period. Reflux was continued for 5 hours after which time the solid which had separated was collected by suction filtration of the hot mixture, washed with methanol, and dried under vacuum at 70° C. to yield tan crystals of 5,7-diamino-1,3-dimethylpyrimido [4,5-c]pyridazin-4(1H)-one (508 mg; 76% of theoretical yield; M.P.>275° C.)

Elemental analysis: Calcd. for C$_8$H$_{10}$N$_6$O: C 46.59%, H 4.89%, N 40.76%. Found: C 46.66%, H 4.98%, N 40.69%.

NMR (DMSO-d$_6$) δ2.14 (s,3H), 3.74 (s,3H), 6.84 (br s,2H)*, 7.72(br.d, 1H, J=4 Hz)*, 8.96 (br d, 1H, J=4 Hz)*. U.V. λmax (CH$_3$OH) 222 nm (ε12,800), 247 (31,100), 306 (11,600).
*=exchangeable with D$_2$O.

Example 9—7-Amino-3-acetoxymethyl-1-methylpyrimido-[4,5-c]pyridazine-4,5 (1H,6H) dione To a stirred, refluxing solution of 6-(1-methylhydrazino)-isocytosine hemihydrate (0.16 g) in methanol (5 ml) was added methyl 3-acetoxy-2-oxo-propanoate (0.19 g). After refluxing for a further 22 hours, the solid formed during the course of the reaction was collected by filtration of the hot reaction mixture and washed with methanol to yield 7-amino-3-acetoxymethyl-1-methylpyrimido [4,5-c]pyridazine-4,5(1H, 6H) dione (0.107 g; 40% of theoretical yield; M.P.>280° C.).

Elemental analysis: Calcd. for C$_{10}$H$_{11}$N$_5$O$_4$: C 45.28%, H 4.18%, N 26.41%. Found: C 45.11%, H 4.24%, N 26.37%.

NMR (TFA) δ2.32 (s,3H), 4.27(s,3H); 5.51 (s,2H), 7.25 (br s,2H).

U.V. λmax (CH$_3$OH) 258 nm (ε37,100) 299.5 (7,400).

Example 10—7-Amino-3-hydroxymethyl-1-methylpyrimido[4,5-c]-pyridazine-4,5(1H,6H) Sodium Salt (I) ($R^1$=CH$_3$;$R^2$=CH$_2$OH; $R^3$=OH; X=O)

To 7-amino-3-acetoxymethyl-1-methylpyrimido[4,5-c]pyridazine-4,5 (1H, 6H) dione (0.100 g) in water (1 ml) was added dropwise with shaking 10% (w/w) aqueous sodium hydroxide (0.25 ml), the orange solution becoming quickly cloudy. The mixture was allowed to stand at room temperature for 30 minutes after which time the off-white granular solid which had formed was collected by filtration, rinsed well with methanol and dried under vacuum at room temperature to yield 7-amino-3-hydroxymethyl-1-methylpyrimido(4,5-c)pyridazine-4,5(1H,6H)dione as its sodium salt (0.082 g; 81% of theoretical yield; M.P.>300° C.).

Elemental analysis: Calcd. for C$_8$H$_8$N$_5$NaO$_3$.H$_2$O: C 36.50%; H 3.83%; N 26.61%; Na 8.73; Found: C 36.55%, H 3.91%, N 26.50%, Na 8.70. NMR (TFA) δ4.29 (s,3H), 5.19 (s,2H), 7.20 (br. s,2H).

U.V. λmax (0.1 N HCl) 255 nm (ε39,400), 299 (7,200).

Example 11: 7-Amino-3-(1-ethoxycarbonylethyl)-1-methylpyrimido[4,5-c]pyridazine-4,5(1H,6H)-dione (I) ($R^1$=CH$_3$; $R^2$=CH(Y)CO$_2$Z, Y=CH$_3$, Z=C$_2$H$_5$; $R^3$=OH; X=O)

To a stirred, refluxing solution of 6-(1-methylhydrazino)-isocytosine hemihydrate (1.86 g) in water (120 ml) was added diethyl 3-methyl-2-oxosuccinate (4.59 g). After refluxing for a further 3 hours, the solid formed during the course of the reaction was collected by filtration of the hot reaction mixture, washed with two portions of water (20 ml each) and dried under vacuum at 70° C. to yield 7-amino-3-(1-ethoxycarbonylethyl)-1-methylpyrimido[4,5-c]pyridazine-4,5(1H, 6H)-dione dione (1.93 g; 58% of theoretical yield; M.P. >280° C.).

Elemental analysis: Calcd. for C$_{12}$H$_{15}$N$_5$O$_4$: C 49.14%; H 5.16%; N 23.88%. Found: C 49.10%, H 5.18%, N 23.62%.

NMR (TFA) δ 1.38 (t,3H), 1.77 (d,3H), 4.28 (s,3H), 4.41 (q,3H), 7.17 (br.s,2H).

U.V. λ max (CH$_3$OH) 257 nm (ε41,100), 299.5 (7,400), 310 (5,600).

EXAMPLE 12—7-Amino-3-(1-carboxyethyl)-1-methylpyrimido-[4,5-c]pyridazine-4,5(1H, 6H)-dione (I) ($R^1$=CH$_3$; $R^2$=CH(Y)CO$_2$Z, Y=CH$_3$, Z=H; $R^3$=OH;

A mixture of 7-amino-3-(1-ethoxycarbonylethyl)-1-methylpyrimido [4,5-c]pyridazine 4,5(1H, 6H)-dione (2.97 g) in 10% (w/w) aqueous sodium hydroxide (67 ml) was swirled vigorously for 25 minutes. Although a complete solution was not obtained during the agitation, a solid began to precipitate after 20 minutes. The mixture was then allowed to stand at room temperature for 1 hour before being chilled at 0° C. for 1½ hours to allow complete precipitation of the product. The precipitate was collected by filtration, washed well with three portions of 95% ethanol (25 ml each) and dried overnight at room temperature in a vacuum desiccator to yield 7-amino-3-(1-carboxyethyl)-1-methyl-pyrimido(4,5-c)pyridazine-4,5(1H, 6H)-dione as its disodium salt (2.42 g; 70% of theoretical yield; M.P.>300; hygroscopic crystals).

Elemental analysis: Calcd. for $C_{10}H_9N_5Na_2O_4 \cdot 0.5\text{-}H_2O$: C 37.74%; H 3.17%; N 22.01%; Na 14.45; Found: C 37.69%, H 3.21%, N 22.05%, Na 14.44.

NMR (TFA) δ 1.81 (d,3H), 4.30 (s,3H), 4.45 (q,1H), 7.17 (br s,2H).

U.V. λmax (0.1 N HCl) 255 nm (ε41,500), 301(7,800).

EXAMPLE 13—7-Amino-1,3-dimethylpyrimido(4,5-c)-pyridazine-4,5(1H, 6H)-dione (I) ($R^1=CH_3$; $R^2=CH_3$; $R^3=OH$: $X=O$)

A mixture of 5,7-diamino-1,3-dimethylpyrimido(4,5-c)pyridazin-4(1H)-one (0.50 g) and 1.5 N aqueous sodium hydroxide (35 ml) was stirred at reflux for 24 hours after which time a small amount of solid was removed by filtration of the hot mixture. On cooling, the yellow filtrate deposited while needles which were collected by filtration and dissolved in warm water (20 ml). Adjustment of this aqueous solution to pH 5 by dropwise addition of 6 N hydrochloric acid and subsequent cooling to room temperature provided a very finely divided white precipitate which was collected, washed with water and dried under vacuum at 70° C. to give 7-amino-1,3-dimethylpyrimido(4,5-c)-pyridazine-4,5(1H, 6H)-dione (0.38 g; 76% of theoretical yield). The U.V., I.R., and N.M.R. spectra of this compound were identical to those of the sample made according to the procedure of Example 7.

EXAMPLE 14—7-Amino-1-methyl-4-phenylpyrimido{4,5-c}pyridazin-5-(1H)-one (I) ($R^1=CH_3$; $R^2=H$; $R^3=C_6H_5$; $X=O$)

To a mixture of 6-(1-methylhydrazino)isocytosine hemihydrate (0.82 g) and methanol (100 ml) stirred at reflux was added 97% phenylglyoxal monohydrate (11.4 g). The immediate formation of a yellow solution was followed by a rapid precipitation. Reflux was continued for 4½ hours before the hot mixture was filtered (suction). The collected solid was washed with methanol and dried under vacuum (70°) to yield, 98 mg of yellow solid.[1] After 2 hours, the yellow needles that had separated from the filtrate were collected, washed with methanol and dried under vacuum (70°), yield 0.63 g of the pure product: m.p. 262.5°-264° d; nmr (CF3COOH) δ4.49 (s, 3H), 7.18 (br s, 2H), 7.60.(s, 5H), 8.72 (s, 1H); uv λmax (1N HCL) 238 nm (ε 18,500), 262 (21,300), 270 sh (19,900), 358 (10,400).

Anal. Calcd for $C_{13}H_{11}N_5O$: C 61.65%, H 4.38%, N 27.65%; Found: C 61.67%, H 4.43%, N 27.76%.

[1]The nmr spectrum suggested that this solid was a 1.2:1.0 mixture of desired product and non-cyclic hydrazone.

EXAMPLE 15—7-Amino-4-(3-hydroxyphenyl)-1-methyl-pyrimido{4,5-c}-pyridazin-5-(1H)-one (I) ($R^1=CH_3$; $R^2=H$; $R^3=C_6H_4OH$; $X=O$)

To a stirred solution of m-hydroxyphenylglyxoal monohydrate[1] (0.90 g) in methanol (100 ml) at room temperature was added 6-(1-methylhydrazino)isocytosine hemihydrate (0.70 g). The mixture was heated to reflux within a 10-minute period to give a yellow solution. Reflux was continued for 3 hours before the yellow solid that precipitated was collected, washed with methanol and dried under vacuum (70°) to yield 1.04 g of crude product shown by nmr to be a 5.5:1 mixture of desired product and its 3-(3-hydroxyphenyl) isomer. Recrystallization[2] of 1.0 g of this mixture from methanol gave 0.41 g. of pure 4-substituted isomer: m.p. >300° C.; nmr (CF3COOH) δ4.49 (s, 3H), 7.18-7.30 m, 7.41 br s nd 7.67 m (6H), 8.69 (s, 1H); uv (1N HCl) λmax 237 nm (ε18,600), 261 (20,800), 357 (8,300).

Anal. Calcd. for $C_{13}H_{11}N_5O_2$: C 57.99%, H 4.12%, N 26.01%; Found: C 57.82%, H 4.14%, N 26.02%.

[1]G. Fodor and O. Kovacs, J. Am. Chem. Soc. 71, 1045 (1949).
[2]A second crop of yellow needles obtained from the recrystallisation was characterized as a 5:2 mixture of 4- to 3-substituted isomers.

Anal. Calcd. for $C_{13}H_{11}N_5O_2$: C 57.99%, H 4.12%, N 26.01%; Found: C 57.75%, H 4.15%, N 25.92%.

EXAMPLE 16—α-{N-(2-Amino-4-oxo-3,4-dihydro-6-pyrimidyl)-N-methylhydrazono}-4-hydroxyacetophenone hydrate (VI) ($R^2=H$; $R^3=C_6H_4OH$)

To a stirred mixture of 6-(1-methylhydrazino)isocytosine hemihydrate (0.82 g) and glacial acetic acid (25 ml) (protected by a drying tube) was added 4-hydroxyphenylglyoxal hydrate (1.26 g) at once. The mixture was stirred at room temperature for 1½ hours before being quickly heated to boiling. Reflux was continued for only 5 minutes, just long enough to effect a complete, dark orange solution. This solution deposited a yellow solid during a 2 hour period at room temperature. The collected solid was washed first with a small quantity of glacial acetic acid and then with ether and dried under vacuum (70° C.), yield, 0.69 g. of the crude product. Recrystallisation of 130 mg from methanol provided 61 mg of the product as a hydrate: m.p. >300; nmr (DMSO-d6) δ3.49 (s, 3H), 5.44 (s, 1H), 6.65 (br s, 2H), 6.87 (d, 2H, J =9Hz), 7.56 (s, 1H), 7.94 (d, 2H, J=9Hz), 10.36 (br s, 2H), and 3.31 (H2O); uv λmax (CH3OH) 228 nm (ε20,000), 255 sh (15,500), 285 (23,900), 310 sh (17,400), 345 (14,100). Mass spectrum (field desorption): m/e 288, 30%; M, m/e 287, 25%; m/e 270, 88%; m/e 166,100%.

Anal. Calcd for $C_{13}H_{13}N_5O_3 \cdot H_2O$: C 51.20%, H 4.95%, N 22.94%; Found: C 50.99%, H 4.98%, N 22.83%.

EXAMPLE 17—7-Amino-4-(4-hydroxyphenyl)-1-methyl-pyrimido{4,5-c}pyridazin-5(1H)one (I) ($R^1=CH_3$; $R^2=H$; $R^3=C_6H_4OH$; $X=O$)

A mixture of crude α-{N-(2-Amino-4-oxo-3,4-dihydro-6-pyrimidyl)-N-methylhydrazono}-4-hydroxyacetophenone hydrate (200 mg) and glacial acetic acid[1] (10 ml) (drying tube) was heated at reflux for 4 hours. A dark solution gradually formed during the first 2 hours; no uv charge was detected after 3 hours. The resulting dark solution, on standing for 3 days at room temperature, deposited orange crystals which were collected by filtration, washed with glacial acetic acid and dried under vacuum (70° C.), yield 124 mg of the pyrmidopyridazinone, 1.75 acetic acid: m.p. >300°; nmr (CF$_3$COOH) δ4.47 (s, 3H), 7.17 (br s, 2H), 7.18 (d, 2H, J=9Hz), 7.63 (d, 2H, J=9Hz), 8.71 (s, 1H) and 2.28 (s, acetic acid, 1.75 mol); uv λmax (1N HCl) 241 nm (ε20,800), 264 (19,600), 384 (10,700). Mass spectrum (70ev, 280°) M, m/e 269, 31%; m/e 268, 100%.

Anal. Calcd. for C$_{13}$H$_{11}$N$_5$O$_2$.1.75 C$_2$H$_4$O$_2$: C 52.94%, H 4.85%, N 18.71%; Found: C 52.80%, H 4.86%, N 18.63%.

[1] Attempts to cyclise this hydrazone in either methanol or methanol/acetic acid at reflux failed.

EXAMPLE 18—7-Amino-3-phenacyl-1-methylpyrimido{4,5-c}pyridazine-4,5 (1H, 6H)-dione (I) (R$^1$=CH$_3$; R$^2$=CH$_2$CO.C$_6$H$_5$; R$^3$=OH; X=O)

To a stirred, refluxing mixture of 6-(1-methylhydrazino)-isocytosine hemihydrate (1.00 g) in methanol (100 ml) was added ethyl benzopyruvate (2.01 g). After 67 hours yellowish-brown solid was collected from the hot reaction mixture, washed with three portions of methanol totalling 20 ml, and dried under vacuum at 75°, yield 0.130 g. (7%): m.p. >300°; nmr (CF$_3$COOH) δ4.28 (s, 3H), 4.87 (s, 2H), 7.17 (br s, 2H9, 7.4–8.3 (m, 5H); uv λmax (CH$_3$OH) 259 nm (δ44,900), 301 (8,300), 310 sh (6,900), 375 sh (900). Mass spectrum (240°): M, m/e 311, 17%; m/e 166, 1%; m/e 105, 100%. The following accurate mass was determined: 166.0487 (C$_6$H$_6$N$_4$O$_2$).

Anal. Calcd. for C$_{15}$H$_{13}$N$_5$O$_3$: C 57.87%, H 4.21%, N 22.50%; Found: C 57.80;, H 4.26%, N 22.46%.

EXAMPLE 19 —7-Amino-3-(3-hydroxyphenacyl)-1-methyl-pyrimido{4,5-c} pyridazine-4,5 (1H, 6H)-dione (I) (R$^1$=CH$_3$; R$^2$=CH$_2$Co.C$_6$H$_4$OH; R$^3$=OH; X=O)

Adopting the general procedure of Example 20, the above compound was synthesised and isolated.

Reaction time of 22 hours, yield 7%: m.p. 290°–295° dec; nmr (CF$_3$COOH) δ4.28 (s, 3H), 4.83 (s, 2H), 7.16 (br s, 2H), 7.4–8.0 (m, 4H); uv λmax (CH$_3$OH) 213.5 nm (ε26,300), 259 (47,400), 303 (10,600), 309 sh (9,700).

Anal. Calcd. for C$_{15}$H$_{13}$N$_5$O$_4$.0.5H$_2$O: C 43.16%; H 5.55%; N 16.78%. Found: C 43.15%, H 5.59%, N 16.83%.

EXAMPLE 20—7-Amino-3-(2,4,6-trimethoxyphenacyl)-1-methyl-pyrimido-{4,5-c}pyridazine-4,5 (1H, 6H)-dione (I) (R$^1$=CH$_3$; R$^2$=CH$_2$CO.C$_6$H$_2$(OCH$_3$)$_3$; R$^3$=OH; X=O)

Adopting the general procedure of Example 20, the above compound was synthesised and isolated.

Reaction time of 19½ hours. Yield 5%: m.p. 280° dec.; nmr (CF$_3$COOH) δ4.18, 4.24, and 4.25 (overlapping s's, 12H), 4.96 (s, 2H), 6.52 (s, 2H), 7.22 (br s, 2H) uv λmax (CH$_3$OH) 258 nm (ε37,500), 296.5 sh (12,700), 311.5 sh (9,800).

Anal. Calcd. for C$_{18}$H$_{19}$N$_5$O$_6$: C 53.86%, H 4.77%, N 17.45%; Found: C 53.68%, H 4.81%, N 17.46%.

EXAMPLE 21—7-Amino-3-(2,5-dimethoxyphenacyl)-1-methyl-pyrimido-{4,5-c}-pyridazine-4,5 (1H, 6H)-dione (I) (R$^1$=CH$_3$; R$^2$=CH$_2$CO.C$_6$H$_3$(OCH$_3$)$_2$; R$^3$=OH; X=O)

To a stirred, refluxing mixture of 6-(1-methylhydrazino)-isocytosine hemihydrate (4.00 g) in methanol (400 ml) was added methyl 2,5-dimethoxybenzoylpyruvate (7.14 g). After 19 hours reddish-orange solid was collected from the hot mixture, washed with two portions of methanol totalling 50 ml, and dried under vacuum at 75° to yield 0.628 g. This solid was an inseparable 1:1 mixture of the desired 4,5-dione and its 3,5-dione isomer.

The filtrate was refluxed an additional 22.5 hours, and pale yellow solid was collected from the hot mixture, washed with several portions of methanol totalling 30 ml, and dried under vacuum at 75°, yield 0.09 g (1%): m.p. >300°; nmr (CF$_3$COOH) δ4.02 (s, 3H), 4.07 (s, 3H), 4.28 (s, 3H), 4.90 (s, 2H), 6.8–7.7 (m, 5H); uv λmax (CH$_3$OH) 223 nm weak sh (ε22,800), 258.5 (48,500), 302.5 (10,000), 311.5 sh (9,000), 332.5 sh (5,500).

Anal. Calcd. for C$_{17}$H$_{17}$N$_5$O$_5$: C 54.98%, H 4.61%, N 18.86%; Found: C 54.68%, H 4.64%, N 19.03%.

EXAMPLE 22—7-Amino-3-(2,4-dimethoxyphenacyl)-1-methyl-pyrimido-{4,5-c}pyridazine, 4,5 (1H, 6H)-dione (I) (R$^1$=CH$_3$; R$^2$=CH$_2$Co.C$_6$H$_3$ (OCH$_3$)$_2$; R$^3$=OH; X=O)

Following the general procedure of Example 23, the above compound was synthesised and isolated.

A 2:1 mixture of 4,5-dione and 3,5-dione isomers, respectively, was collected after 18 hours. The filtrate was refluxed an additional 47 hours for a 9% yield of 4,5-dione isomer: m.p. 290°–300° dec; nmr (CF$_3$COOH) δ4.02 and 4.06 (overlapping s's, 6H), 4.27 (s, 3H), 4.84 (s, 2H), 6.6–8.2 (m, 5H); uv λmax (CH$_3$OH) 227.5 nm (ε20,200), 259.5 (40,700), 403 (17,400), 413 (2,800), 435 (2,700), 460 (2,900).

Anal. Calcd. for C$_{17}$H$_{17}$H$_5$O$_5$: C 54.98%, H 4.61%, N 18.86%; Found C 54.97%, H 4.69%, N 18.98%.

EXAMPLE 23—7-Amino-3-(3,4-dimethoxyphenacyl-1-methyl-pyrimido{4,5-c}pyridazine-4,5-(1H, 6H)-dione (I) (R$^1$=CH$_3$; R$^2$=CH$_2$CO.C$_6$H$_3$(OCH$_3$)$_2$; R$^3$=OH; X=O)

Following the general procedure of Example 23, the above compound was synthesised and isolated.

An insoluble mixture was collected after 17 hours. The filtrate was refluxed an additional 47 hours for a 2% yield of 4,5-dione isomer: m.p. >300°; nmr (CF$_3$COOH) δ4.04 and 4.08 (overlapping s's, 6H), 4.28 (s, 3H), 4.83 (s, 2H9, 7.0–7.4 (m, 3H), 7.7–8.2 (m, 2H); uv λmax (CH$_3$OH) 229 nm (ε23,300), 259 (42,000), 274 sh (22,200), 304 (18,700).

Anal. Calcd. for C$_{17}$H$_{17}$N$_5$O$_5$.0.1H$_2$O: C 54.72%, H 4.65%, N 18.77%; Found: C 54.71%, H 4.68%, N 18.71.

EXAMPLE 24—7-Amino-3-(3,4,5-trimethoxyphenacyl)-1-methyl-pyrimido-{4,5-c}pyridazine-4,5 (1H, 6H)-dione (I) ($R^1$=$CH_3$; $R^2$=$CH_2CO.C_6H_2$ ($OCH_3$)$_3$; $R^3$=OH; X=O)

Following the general procedure of Example 23, the above compound was synthesised and isolated.

A 1:1 mixture of 4,5-dione and 3,5-dione isomers, respectively, was collected after 18½ hours. The filtrate was refluxed an additional 23 hours for a 2% yield of 4,5-dione isomer: m.p. >300°; nmr ($CF_3COOH$) ε4.07 and 4.13 (overlapping s's, 9H), 4.30 (s, 3H), 4.86 (s, 2H), 7.18 (br s, 2H), 7.54 (s, 2H); uv λmax ($CH_3OH$) 213 nm (ε32,500), 285.5 (43,700), 297 sh (17,200), 310 sh (13,700). Mass spectrum (250°): M, m/e 401, 7%; m/e 195, 100%; m/e 166,2%. The following accurate mass was determined: 166.0488 ($C_6H_6N_4O_2$).

Anal. Calcd. for $C_{18}H_{19}N_5O_6$: C 53.86%, H 4.77%, N 17.45%; Found C 53.82%, H 4.85%, N 17.55%.

EXAMPLE 25—7-Amino-1-methyl-4-(3,4,5-trimethoxyphenacyl)-pyrimido-{4,5-c}pyridazine-3,4-(1H, 6H)-dione (XII) ($R^1$=$CH_3$; $R^8$=$CO.C_6H_2(OCH_3)_3$)

To a stirred, refluxing solution of 6-(1-methylhydrazino)-isocytosine hemihydrate (4.00 g) in methyl cellosolve (400 ml) was added 8.64 (0.0292 mol) of methyl 3,4,5-trimethoxybenzoylpyruvate*. After 1 hour 50 minutes reddish-orange solid was collected from the hot mixture, washed with three portions of methanol totalling 150 ml, and dried under vacuum at 75°, yield 4.29 g (44% theoretical): m.p. >300°; nmr ($CF_3COOH$) δ4.08 and 4.13 (overlapping s's, 9H), 4.33 (s, 3H), 5.39 (s, 2H), 6.96 (br s, 2H), 7.54 (s, 2H); uv λmax ($CH_3OCH_2CH_2OH$) 248.5 nm (ε18,700), 268 sh (18,300), 271.5 (18,500), 317.5 (8,900), 388.5 weak sh (4,400), 413 sh (6,800), 464 sh (33,300), 486 (42,500). Mass spectrum (field desorption M, m/e 401.

Anal. Calcd. for $C_{18}H_{19}N_5O_6$- C 53.86%, H 4.77%, N 17.45%; Found: C 53.75%, H 4.80%, N 17.58%.

*Made from 3,4,5-trimethoxyacetophenone and methyl oxalate in the presence of methanolic sodium methoxide.

EXAMPLE 26—7-Amino-1,4-dimethylpyrimido{4,5-c}pyridazine-3,5-(1H, 2H)-dione (I) ($R^1$=$CH_3$; $R^2$=OH; $R^3$=$CH_3$; X=O)

7-Amino-1-methyl-4-(3,4,5-trimethoxyphenacyl)-pyrimido {4,5-c}pyridazine-3,5 (1H, 2H)-dione (1.0 g) was dissolved in N NaOH (40 ml). After 17½ hours the green solution was brought to neutrality with concd. HCl. Yellowish-green solid was collected, washed with two portions of water totalling 40 ml, and dried under vacuum at 75°, yield 0.500 g.

The product was stored for three days under 60 ml of ether, pulverised, collected, and dried under vacuum at 75° C., yield 0.488 g (85% theoretical): m.p. >300°; nmr ($CF_3COOH$) δ3.03 (s, 3H), 4.27 (s, 3H), 6.85 (br s, 2H); uv λmax (N NaOH) 258.5 nm (ε32,800), 282.5 sh (7,500), 402 (5,200). Mass spectrum (310°): M, m/e 207, 100%; m/e 206, 7%. The following accurate masses were determined: 207.0772 ($C_8H_9N_5O_2$), 206.0701 ($C_8H_8N_5O_2$).

Anal. Calcd. for $C_8H_9N_5O_2.0.75H_2O$: C 43.53%, H 4.80%, N 31.73%; Found: C 43.61%, H 4.72%, N 31.59%.

EXAMPLE 27—7-Amino-1-methylpyrimido{4,5-c}pyridazine-3,5 (1H, 2H)-dione (I) ($R^1$=$CH_3$; $R^2$=OH; $R^3$=H; X=O)

To a stirred, refluxing solution of 6-(1-methylhydrazino)-isocytosine hemihydrate (3.00 g) in a solvent mixture consisting of methanol (75 ml) and water (75 ml) was added ethyl diethoxyacetate (3.89 g) and concd. HCl (1.8 ml). After 18½ hours brownish-orange solid was collected, washed with 1:1 $H_2O$:MeOH (10 ml) and methanol (10 ml), and dried under vacuum at 75° to yield 1.71 g. This solid was shown by nmr ($CF_3COOH$) to be a 3:1 mixture of intermediate carboxylic acid hydrazone and desired cyclic product, respectively.

A sample of this solid (1.665 g) was stirred for 1 hour in N HCl (225 ml). Undissolved solid (shown by nmr to be a 20:1 mixture of hydrazone and desired cyclic product, respectively) was collected. The filtrate was brought to pH 3 with 4 N NaOH, and orange solid was collected, washed with water (5×3 ml) and dried under vacuum at 75° C., yield 0.497 g.

This crude product was partially purified by dissolution in N HCl (300 ml) followed by partial neutralization with 4N NaOH. At pH 1 a small amount of solid was removed by filtration. At pH 2 an additional small amount of solid was removed by filtration. The filtrate was brought to pH 3, and orange solid was collected, washed with water (3×5 ml), and dried under vacuum at 70° to yield 0.424 g.

This solid was then redissolved in N HCl (295 ml), and after 1 hour the solution was filtered. The filtrate was brought up to pH 1 with 4 N NaOH, and a small amount of solid was removed by filtration. The pH of the filtrate was brought to 3 and then 6, and orange solid was collected, washed with water (3×5 ml), and dried under vacuum at 70° to yield 0.238 g (7% theoretical): m.p. >300°; nmr ($CF_3COOH$) δ4.33 (s, 3H), 7.08 (br s, 2H), 8.36 (s, 1H); uv λmax (N NaOH) 260 nm (ε31,300), 413 (5,400). Mass spectrum (360°): M, m/e 193, 94%; m/e 165, 100% (M-CO).

Anal. Calcd. for $C_7H_7N_5O_2$: C 43.52%, H 3.65%, N 36.25%; Found: C 43.27%, H 3.62%, N 36.02%.

EXAMPLE 28

Adopting the general procedure of Example 7, that is to say, addition of the appropriate α-ketoester to a refluxing mixture or solution prepared from a very pure, appropriately substituted alkylhydrazinoisocytosine of formula (III) and filtered solvent in the proportion of 1 g. in 100 ml., collection by filtration of the precipitated compound of formula (I) fronm the hot reaction mixture, washing with a small portion of fresh reaction solvent and drying under vacuum at 70°, the following compounds of formula (I) were prepared (see Table 1):

TABLE 1

| COMPOUND OF FORMULA (I) | | | | Molar Ratio | Reflux Solvent | | ELEMENTAL ANALYSIS. |
| --- | --- | --- | --- | --- | --- | --- | --- |
| $R^1$ | $R^2$ | $R^3$ | X | (V:IV) | & Reflux time | Yield(%) | F = Found Ca = Calculated |
| $CH_3$ | CH(Y)$CO_2$Z | OH | O | 1.7:1 | $CH_3OH$ | 37 | Ca:-C47.31% H4.69% N25.08% |

TABLE 1-continued

| COMPOUND OF FORMULA (I) | | | | Molar Ratio | Reflux Solvent | | ELEMENTAL ANALYSIS. |
| --- | --- | --- | --- | --- | --- | --- | --- |
| $R^1$ | $R^2$ | $R^3$ | X | (V:IV) | & Reflux time | Yield(%) | F = Found  Ca = Calculated |
| | Y = H, Z = $C_2H_5$ | | | | 48 hrs. | | F:-C47.40% H4.78% N25.01% |
| $CH_3$ | $CH(Y)CO_2Z$ | OH | O | 1.2:1 | $CH_3OH$ | 56 | Ca:-C57.46% H4.82% N19.71% |
| | Y = $CH_2C_6H_5$ | | | | 69 hrs. | | F:-C57.36% H4.88% N19.56% |
| | Z = $CH_3$ | | | | | | |
| $CH_3$ | $CH_2C_6H_5$ | OH | O | 1.1:1 | $CH_3OH$ | 53 | Ca:-C59.35% H4.63% N24.72% |
| | | | | | (under $N_2$) | | F:-C59.33% H4.65% N24.65% |
| | | | | | 42 hrs. | | |
| $CH_3$ | $CH_2C_6H_4(NO_2)$ | OH | O | 1.5:1 | $CH_3OH$ | 40 | Ca:-C51.22% H3.68% N25.60% |
| | | | | | 26 hrs. | | F:-C51.20% H3.71% N25.58% |
| $CH_3$ | $CH_2C_6H_3(OCH_3)_2$ | OH | O | 1.5:1 | $CH_3OH$ | 38 | Ca:-C55.97% H4.99% N20.40% |
| | | | | | (under $N_2$) | | F:-C56.07% H5.06% N20.27% |
| | | | | | 42 hrs. | | |
| $C_2H_5$ | $CH_3$ | OH | O | 1.25:1 | $H_2O$ | 74 | Ca:-C48.86% H5.01% N31.66% |
| | | | | | 1 hr. | | F:-C48.79% H5.04% N31.47% |
| $C_2H_4OH$ | $CH_3$ | OH | O | 2:1 | $H_2O$ | 61 | Ca:-C45.57% H4.67% N29.53% |
| | | | | | 1½ hrs. | | F:-C45.66% H4.72% N29.38% |
| n-$C_4H_9$ | $CH_3$ | OH | O | 2:1 | $H_2O$ | 80 | Ca:-C53.00% H6.07% N28.10% |
| | | | | | 4 hrs. | | F:-C53.07% H6.12% N28.00% |
| $CH_2C_6H_5$ | $CH_3$ | OH | O | 2.5:1 | $H_2O$ | 87 | Ca*:-C57.52% H4.83% N23.96% |
| | | | | | 23 hrs. | | F:-C57.30% H4.85% N23.74% |

*For the hemihydrate

EXAMPLE 29—7-Amino-1,3,4-trimethylpyrimido(4,5-c)pyridazin-5(1H)-one

To a stirred, refluxing mixture of 6-(1-methylhydrazino)isocytosine hemihydrate (1.62 g) in methanol (150 ml) was added at once diacetyl (1.8 ml). After 19 hours, a brown solid was collected, washed with methanol (5 ml) and dried under vacuum at 70°; yield, 2.02 g of crude pyrimidopyridazinone, suggested by nmr to be over 90% pure. Obtained as needles by recrystallisation from glacial acetic acid in a nitrogen atmosphere and dried under vacuum at 25°, the product was characterised as the pyrimidopyridazinone. 2.47 $CH_3COOH$: mp>300°; nmr ($CF_3COOD$) δ2.78 (s, 3H), 3.09 (s, 3H), 4.42 (s, 3H) and 2.28 (s, acetic acid, 2.5 mol); uv λmax ($CH_3OH$) 245 nm (ε21,000), 261 (17,400), 266 sh (16,100), 332 sh (3,700), 370 (4,800). Mass spectrum (330°): M. m/e 205, 100%; m/e 177, 18%; m/e 163, 44%.

Anal. Calcd. for $C_9H_{11}N_5O$. 2.47 $CH_3COOH$: C 47.36%; H 5.95%; N 19.81%. Found: C 47.26%; H 5.98%; N 19.85%.

EXAMPLE 30—5,7-Diamino-1-methyl-3-(3,4,5-trimethoxybenzoyl)-methylpyrimido(4,5-c)pyridazin-4(1H)-one To a stirred, refluxing solution of 2,4-diamino-6-(1-methylhydrazino)pyrimidine (1.54 g) in absolute ethanol (150 ml; drying tube) was added methyl 2,4-dioxo-4-(3,4,5-trimethoxyphenyl)-n-butyrate (4.45 g). After 4 hours, the resulting mixture was filtered to remove an uncharacterised solid (0.17 g). The filtrate was refluxed for an additional 22 hours before more unidentified solid (0.09 g) was removed by filtration. The filtrate was heated at reflux for another 3 hours to give a precipitate which was collected by filtration, washed with ethanol and dried under vacuum at 70°, yield 0.31 g (7.7% of theoretical) of pure pyrimidopyridazinone, a white solid: mp>300°; nmr ($CF_3COOH$) δ4.05 sh, 4.10 s (12 H), 4.69 (s, 2H), 7.50 (s, 2H), 8.45 (br s, 2H); uv λmax ($CH_3OH$) 218.5 nm (ε35,700), 248 (31,700), 256 (27,600), 304 (20,600). Mass spectrum (180°): M, m/e 400, 23%; m/e 205, 1.5%; m/e 195, 100%.

Anal. Calcd. for $C_{18}H_{20}N_6O_5$: C 53.99%; H 5.03%; N 20.99%. Found: C 53.98%; H 5.06%; N 20.97%.

EXAMPLE 31

A. Compounds of formula (I) were tested for anticoccidial activity in vivo in combination with diaveridine (DV) and sulphaquinoxaline (SQ), each at 20 ppm, according to the following procedure.

Groups of five, seven day old chicks were each infected orally with 100,000 sporulated oocysts of the Weybridge strain of E. tenella. Drugs were administered as a mixture in LD5 chick mash deficient in vitamin K, beginning one day prior to infection and continuing for 8 days. On the sixth day after infection, caecal lesions of surviving chicks were scored on a scale of 0, 1, 2 or 3 and any dead chicks with lesions were scored as 4. The activity of drugs is expressed as follows for each group:

+++ = mean lesion score of 0.0 to 0.9
++ = mean lesion score of 1.0 to 1.9
+ = mean lesion score of 2.0 to 3.4

The following results were obtained:

| Compound of formula (I) | | | | Activity |
| --- | --- | --- | --- | --- |
| $R^1$ | $R^2$ | $R^3$ | X | (conc. in p.p.m.) |
| $CH_3$ | $CH_2C_6H_4NO_2(2)$ | OH | O | + (180) |
| | | | | + (60) |
| | | | | + (20) |
| $C_2H_5$ | $CH_3$ | OH | O | + (180) |
| | | | | (60) |
| | | | | (20) |

B. Compounds of formula (I) were also tested for anticoccidial activity in vivo in combination with DV (20 p.p.m.) and SQ (20 p.p.m.) as under (A) (vide supra), but using an infection of 6,000 sporulated oocysts per chick; the procedures were otherwise identical.

The following results were obtained:

| Compound of formula (I) | | | | Activity |
|---|---|---|---|---|
| $R^1$ | $R^2$ | $R^3$ | X | (conc. in p.p.m.) |
| $CH_3$ | $CH_2$-C₆H₃(OCH₃)(OCH₃) | OH | O | +++ (200) (20) (5) |
| $CH_3$ | $CH_2C(O)$-C₆H₃(OCH₃)(OCH₃) | OH | O | ++ (200) |
| $CH_3$ | $CH_3$ | OH | O | ++ (200) |
| $CH_3$ | $CH_2OH$ | OH | O | ++ (200) |
| $CH_3$ | $CH_2CO_2C_2H_5$ | OH | O | ++ (200) |

EXAMPLE 32

The anticoccidial activity of compounds of formula (I) in combination with a mixture of diaveridine and sulphaquinoxaline in vitro against *E. tenella* was tested using standard techniques. The following results were obtained wherein activity is expressed as follows:
5=No parasite development
4=1–25% parasite development
3=26–50% parasite development
2=51–75% parasite development
1=76–95% parasite development
0=95–100% parasite development

TABLE 2

| COMPOUND OF FORMULA I | | | | Activity (concentration μg/ml). |
|---|---|---|---|---|
| $R^1$ | $R^2$ | $R^3$ | X | |
| $CH_3$ | $CH_3$ | OH | O | 2(100) 1(25) 0(6.25) |
| $CH_3$ | $CH_2OH$ | OH | O | 3(100) 0(25) |
| $CH_3$ | $CH(Y)CO_2Z$ Y = H; Z = $C_2H_5$ | OH | O | 4(100) 1(25) 0(6.25) |
| $CH_3$ | $CH(Y)CO_2Z$ Y = $CH_3$; Z = H | OH | O | 1(100) 0(25) |
| $CH_3$ | $CH(Y)CO_2Z$ Y = $CH_3$; Z = $C_2H_5$ | OH | O | 2(100) 0(25) |
| $CH_3$ | $-CH_2$-C₆H₃(OCH₃)(OCH₃) | OH | O | 5(100) 3(25) 2(6.25) |
| $CH_3$ | $-CH_2-C(O)$-C₆H₃(OCH₃)(OCH₃) | OH | O | 4(100) 2(25) 3(6.25) 2(1.56) |
| $CH_3$ | $-CH_2-C(O)$-C₆H₃(OCH₃)(OCH₃) with O-CH₃ | OH | O | 5(100) 3(25) 2(6.25) 2(1.56) |
| $CH_3$ | $-CH_2-C(O)$-C₆H₂(OCH₃)(OCH₃)(OCH₃) | OH | O | 1(100) 0(25) |
| $CH_3$ | $-CH_2C_6H_5$ | OH | O | 4(25) 2(6.25) |
| $C_2H_4OH$ | $CH_3$ | OH | O | 1(100) |

TABLE 2-continued

| COMPOUND OF FORMULA I | | | | Activity (concentration μg/ml). |
|---|---|---|---|---|
| $R^1$ | $R^2$ | $R^3$ | X | |
| $CH_2C_6H_5$ | $CH_3$ | OH | O | 1(25) 0(6.25) 2(25) 0(6.25) |
| n-$C_4H_9$ | $CH_3$ | OH | O | 4(25) 2(6.25) |
| $CH_3$ | $CH_3$ | OH | NH | 3(100) 3(25) 1(6.25) |
| $CH_3$ | $-CH_2-C(O)$-C₆H₂(OCH₃)(OCH₃)(OCH₃) | OH | NH | 3(100) 1(25) |
| $CH_3$ | OH | $CH_3$ | O | 4(25) 2(6.25) |
| $CH_3$ | $CH_3$ | $CH_3$ | O | 3(25) 0(6.25) |
| $CH_3$ | H | $C_6H_5$ | O | 4(25) 2(6.25) |
| $CH_3$ | H | $C_6H_4OH$ | O | 4(25) 2(6.25) |

EXAMPLE 33

Following the procedure of Example 32, compounds of formula (I) were tested for anti-coccidial activity alone in vitro. The following results were obtained:

| COMPOUNDS OF FORMULA I | | | | |
|---|---|---|---|---|
| $R^1$ | $R^2$ | $R^3$ | X | Activity (concentration μg/ml) |
| $CH_3$ | $CH_3$ | OH | O | 2(100) 1(25) 0(6.25) |
| $C_2H_4OH$ | $CH_3$ | OH | O | 1(100) 1(25) |
| n-$C_4H_9$ | $CH_3$ | O | O | 3(25) 1(6.25) |
| $CH_3$ | OH | $CH_3$ | O | 2(28) 1(6.25) |
| $CH_3$ | H | $C_6H_5$ | O | 3(25) 0(6.25) |
| $CH_3$ | H | $C_6H_4OH$ | O | 3(25) 2(6.25) |

What we claim is:

1. A compound of the formula (I)

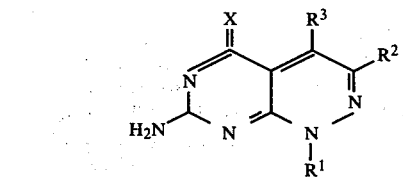

or a tautomer or a non-toxic salt thereof acceptable to animals, wherein $R^1$ is benzyl, or lower alkyl optionally substituted by hydroxy; $R^2$ is hydrogen, hydroxy, methyl, hydroxymethyl, benzyl optionally substituted in the phenyl ring with nitro or one or two lower alkoxy, phenacyl optionally substituted in the phenyl ring with hydroxy or lower alkoxy, —CH(Y)CO$_2$Z in which Y is hydrogen, lower alkyl, or benzyl, and Z is hydrogen or lower alkyl; R$^3$ is hydroxy, methyl, or phenyl optionally substituted with hydroxy; and X is oxygen or NH: provided that:

(i) R$^3$ is methyl only when R$^2$ is methyl or hydroxy;
(ii) R$^3$ is phenyl optionally substituted with hydroxy only when R$^2$ is hydrogen;
(iii) when R$^3$ is hydroxy, R$^2$ is other than hydrogen; and
(iv) R$^2$ and R$^3$ are not both hydroxy.

2. A compound according to claim 1 wherein R$^1$ is lower alkyl optionally substituted with hydroxy; R$^2$ is hydrogen, methyl, hydroxy, phenacyl optionally substituted in the phenyl ring with one hydroxy, or CH(Y)CO$_2$Z in which Y is benzyl, and Z is lower alkyl; and X is oxygen.

3. A compound according to either claim 1 or 2 wherein R$^1$ is methyl; R$^2$ is methyl or hydrogen and R$^3$ is hydroxy or phenyl optionally substituted with hydroxy.

4. A compound according to claim 1 wherein R$^1$ is lower alkyl optionally substituted with hydroxy, or benzyl; and Z is hydrogen or lower alkyl.

5. A compound according to either claim 1 or 4 wherein R$^1$ is methyl or n-butyl and R$^2$ is hydrogen, hydroxy, methyl, benzyl optionally substituted in the phenyl ring with two methoxy, or phenacyl substituted in the phenyl ring with two methoxy.

6. The compound of claim 1 which is 7-amino-1,3-dimethyl-4-oxo-5-hydroxy-1,4-dihydropyrimido(4,5-c)pyridazine, or a tautomer or a non-toxic salt thereof acceptable to animals.

7. The compound of claim 1 which is 7-amino-3-(3,4-dimethoxybenzyl)-5-hydroxy-1-methyl-4-oxo-1,4-dihydropyrimido(4,5-c)pyridazine, or a tautomer or a non-toxic salt thereof acceptable to animals.

8. The compound of claim 1 which is 7-amino-1-n-butyl-5-hydroxy-3-methyl-4-oxo-1,4-dihydropyrimido(4,5-c)pyridazine, or a tautomer or a non-toxic salt thereof acceptable to animals.

9. The compound of claim 1 which is 5,7-diamino-1,3-dimethyl-4-oxo-1,4-dihydropyrimido(4,5-c)pyridazine, or a tautomer or a non-toxic salt thereof acceptable to animals.

10. The compound of claim 1 which is 7-amino-3-(3,4-dimethoxybenzoyl)methyl-5-hydroxy-1-methyl-4-oxo-1,4-dihydropyrimido(4,5-c)pyridazine, or a tautomer or a non-toxic salt thereof acceptable to animals.

11. The compound of claim 1 which is 7-amino-3-benzyl-5-hydroxy-1-methyl-4-oxo-1,4-dihydropyrimido(4,5-c)pyridazine, or a tautomer or a non-toxic salt thereof acceptable to animals.

12. The compound of claim 1 which is 7-amino-3-(2,4-dimethoxybenzoyl)methyl-5-hydroxy-1-methyl-4-oxo-1,4-dihydropyrimido(4,5-c)pyridazine, or a tautomer or a non-toxic salt thereof acceptable to animals.

13. The compound of claim 1 which is 7-amino-1,4-dimethyl-3,5-dioxo-1,2,3,5-tetrahydropyrimido(4,5-c)pyridazine, or a tautomer or a non-toxic salt thereof acceptable to animals.

14. The compound of claim 1 which is 7-amino-5-oxo-1,3,4-trimethyl-1,5-dihydropyrimido(4,5-c)pyridazine, or a tautomer or a non-toxic salt thereof acceptable to animals.

15. The compound of claim 1 which is 7-amino-1-methyl-5-oxo-4-phenyl-1,5-dihydropyrimido(4,5-c)pyridazine, or a tautomer or a non-toxic salt thereof acceptable to animals.

16. The compound of claim 1 which is 7-amino-4-(4-hydroxyphenyl)-1-methyl-5-oxo-1,5-dihydropyrimido(4,5-c)pyradazine, or a tautomer or an non-toxic salt thereof acceptable to animals.

17. A veterinary composition for the treatment of coccidiosis which comprises a non-toxic, effective anticoccidial treatment amount of a compound of the formula (I), or a tautomer or veterinary acceptable salt thereof, as defined in claim 1 herein, together with a veterinary acceptable carrier.

18. A veterinary composition according to claim 17 in unit dose form.

19. A poultry feed which comprises a non-toxic effective anticoccidial treatment amount of a compound of the formula (I), or a tautomer or salt thereof as defined in claim 1.

20. A method of treating coccidiosis in poultry which comprises orally administering to coccidiosis infected poultry an effective coccidiosis treatment amount of the compound, or a tautomer or salt thereof as defined in claim 1.

* * * * *